United States Patent
Brodbeck et al.

(10) Patent No.: US 12,156,687 B2
(45) Date of Patent: Dec. 3, 2024

(54) INSTRUMENT WITH A MULTISTREAM INSTRUMENT HEAD FOR ARGON PLASMA COAGULATION

(71) Applicant: Erbe Elektromedizin GmbH, Tübingen (DE)

(72) Inventors: Achim Brodbeck, Metzingen (DE); Charlotte Herrberg, Bodelshausen (DE); Thomas Staebler, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 520 days.

(21) Appl. No.: 16/001,749

(22) Filed: Jun. 6, 2018

(65) Prior Publication Data
US 2018/0353233 A1 Dec. 13, 2018

(30) Foreign Application Priority Data
Jun. 7, 2017 (EP) .................................. 17174743

(51) Int. Cl.
*A61B 18/14* (2006.01)
*A61B 18/04* (2006.01)
(Continued)

(52) U.S. Cl.
CPC ............. *A61B 18/042* (2013.01); *H05H 1/46* (2013.01); *A61B 18/00* (2013.01);
(Continued)

(58) Field of Classification Search
CPC ..... A61B 18/042; A61B 18/00; A61B 18/082; A61B 2018/00589; A61B 2018/048; A61B 2018/1253; H05H 1/46; H05H 2007/4645
See application file for complete search history.

(56) References Cited

U.S. PATENT DOCUMENTS 4,060,088 A * 11/1977 Morrison, Jr. ....... A61B 18/042
219/121.36
7,628,788 B2 * 12/2009 Datta ................. A61B 18/1492
606/41
(Continued)

FOREIGN PATENT DOCUMENTS

CN 1874732 A 12/2006
CN 101170958 A 4/2008
(Continued)

OTHER PUBLICATIONS

European Search Report for corresponding European Application No. 17174743.9, dated Nov. 20, 2017, 9 pages.
(Continued)

*Primary Examiner* — Jaymi E Della
(74) *Attorney, Agent, or Firm* — Fitch, Even, Tabin & Flannery LLP

(57) ABSTRACT

An instrument for electrosurgical treatment including an instrument head which forms a conveying body with a gas-fillable lumen. The lumen is connected to at least one first opening and at least one second opening in the instrument head. A primary stream of gas leaves through the first opening. The second opening is arranged such that a secondary stream exits the second opening next to the primary stream and/or with additional secondary streams out of additional second openings—away from the instrument head, at least partially peripherally surrounding the primary stream. An electrode is located in the flow of gas exiting out of the first opening for igniting a plasma between the first opening and the tissue to be treated. Due to the secondary stream accompanying the primary stream, an ignition of the plasma is successful even if the instrument is at a relatively large distance from the tissue.

14 Claims, 8 Drawing Sheets

(51) Int. Cl.
    *H05H 1/46*      (2006.01)
    *A61B 18/00*     (2006.01)
    *A61B 18/08*     (2006.01)
    *A61B 18/12*     (2006.01)

(52) U.S. Cl.
    CPC .............. *A61B 2018/00589* (2013.01); *A61B 2018/048* (2013.01); *A61B 18/082* (2013.01); *A61B 2018/1253* (2013.01); *H05H 1/4645* (2021.05)

(56) References Cited

U.S. PATENT DOCUMENTS

| | | | |
|---|---|---|---|
| 7,717,911 B2 | 5/2010 | Schnitzler | |
| 9,125,662 B2 | 9/2015 | Shelton, IV | |
| 10,299,849 B2 | 5/2019 | Cosmescu | |
| 2001/0034519 A1* | 10/2001 | Goble | A61B 18/042 606/41 |
| 2002/0058938 A1 | 5/2002 | Cosmescu | |
| 2003/0028189 A1 | 2/2003 | Woloszko et al. | |
| 2003/0105458 A1 | 6/2003 | Platt | |
| 2004/0044342 A1 | 3/2004 | Mackay | |
| 2008/0039834 A1 | 2/2008 | Mackay | |
| 2008/0215045 A1* | 9/2008 | Platt | A61B 18/042 606/40 |
| 2009/0024122 A1* | 1/2009 | Fischer | A61B 18/042 600/104 |
| 2009/0121637 A1 | 5/2009 | Laroussi | |
| 2011/0288547 A1 | 11/2011 | Morgan | |
| 2011/0301412 A1* | 12/2011 | Cho | A61N 1/44 606/41 |
| 2012/0065635 A1* | 3/2012 | Konesky | A61B 18/042 606/41 |
| 2012/0172789 A1* | 7/2012 | Fischer | A61B 18/042 604/24 |
| 2013/0090644 A1* | 4/2013 | Williams | A61B 18/042 606/49 |
| 2017/0071653 A1 | 3/2017 | Enderle | |
| 2018/0085155 A1* | 3/2018 | Konesky | A61B 18/042 |
| 2019/0090339 A1* | 3/2019 | Frame | A61B 18/042 |

FOREIGN PATENT DOCUMENTS

| | | |
|---|---|---|
| CN | 105120782 A | 12/2015 |
| CN | 105555215 A | 5/2016 |
| CN | 106510838 A | 3/2017 |
| DE | 102005021304 A1 | 11/2006 |
| EP | 1090597 A1 | 4/2001 |
| EP | 3141203 A1 | 3/2017 |
| GB | 2495400 A | 4/2013 |
| JP | S62-028084 A | 2/1987 |
| JP | 2002301088 A | 10/2002 |
| JP | 2008-543355 A | 12/2008 |
| RU | 2642268 C2 | 1/2018 |
| SU | 207289 A1 | 11/1968 |
| WO | 0160273 A1 | 8/2001 |

OTHER PUBLICATIONS

J. Winter et al. "Challenges and solutions on the way to a deployable plasma endoscope" 6th International Conference on Plasma Medicine ICPM 6), Sep. 4-9, 2016, Bratislava, Slovakia.
Chinese First Office Action & Search Report dated Aug. 28, 2020, in corresponding Chinese Application No. 201810573784.5, with English translation (15 pages).
Russian Office Action and Search Report dated Apr. 14, 2021, in corresponding Russian Application No. 2018119933/14(031380), with machine English translation (21 pages).
Japanese Office Action dated Oct. 5, 2021, in Japanese Application No. 2018-109166, with English translation (8 pages).
Chinese Third Office Action dated Jul. 7, 2021, in Chinese Application No. 201810573784.5, with English machine translation (6 pages).
Korean Intellectual Property Office, Decision of Patent Grant in corresponding Korean Application No. 10-2018-0064223, dated Mar. 28, 2023; 3 pages.

* cited by examiner

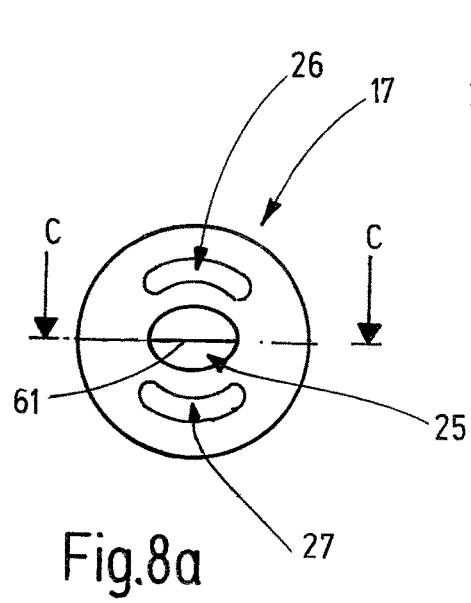
Fig.8a
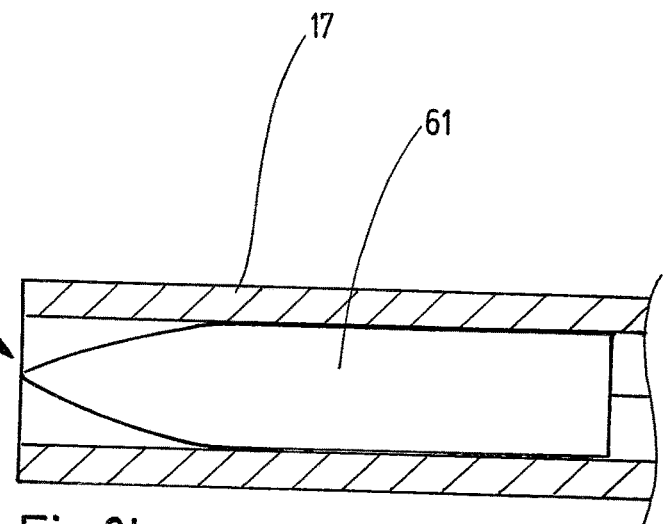
Fig.8b
Fig.8c
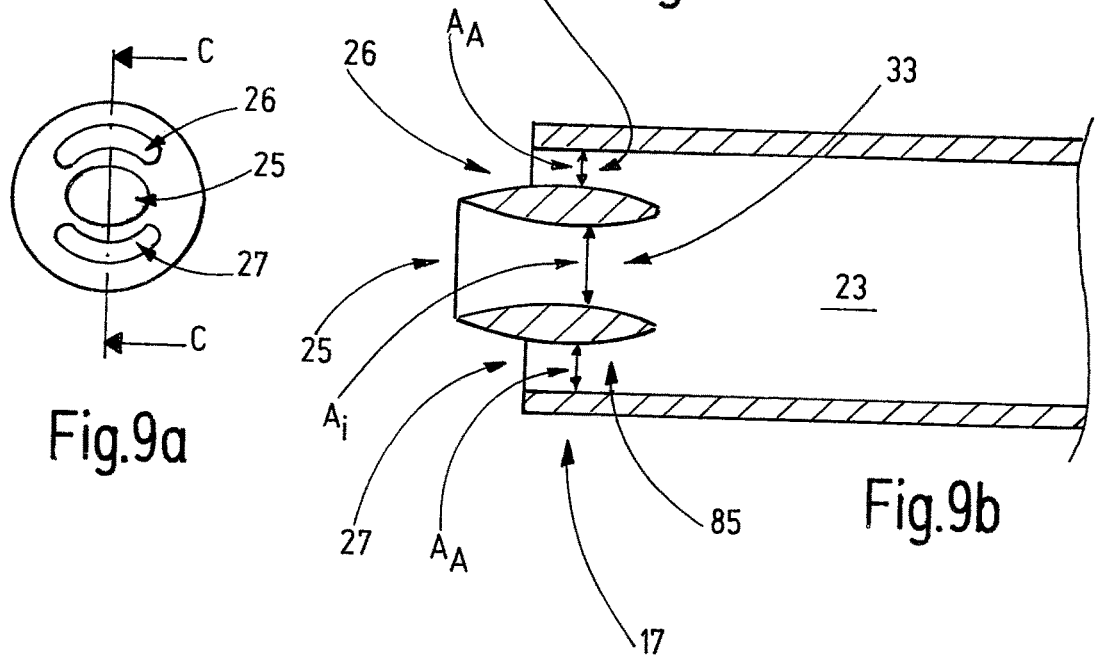
Fig.9a
Fig.9b

INSTRUMENT WITH A MULTISTREAM INSTRUMENT HEAD FOR ARGON PLASMA COAGULATION

RELATED APPLICATION

This application claims the benefit of European Patent Application No. 17174743.9, filed Jun. 7, 2017, the contents of which is incorporated herein by reference as if fully rewritten herein.

TECHNICAL FIELD

The invention relates to an instrument for argon plasma coagulation.

BACKGROUND

In monopolar argon plasma coagulation (APC), the distal end of an instrument is brought near the tissue to be treated, and ionized argon gas is ignited between an electrode on the distal end of the instrument and the tissue surface, so that a plasma beam is formed as a result of this. With the use of the plasma beam it is possible to generate a thermal tissue effect without contact between the distal end of the instrument and the tissue. In particular, it is possible to thus devitalize the tissue or to achieve hemostasis. The ignition distance refers to the distance up to which the instrument needs to be moved toward the tissue for a successful ignition of the plasma to take place.

A large ignition distance is desirable to ensure a reliable ignition of a plasma, even at larger distances. The ignition distance should also be large under influences that reduce the ignition distance, e.g., fluids or moisture in the working area. Even in the event of changes of the distance between the distal end of the instrument and the tissue, a large ignition distance allows a continuous treatment. This is of advantage in particular for a continuous APC treatment of large-area tissue surfaces because, during use, the distance from the tissue and the local ignition conditions can vary greatly. An instrument with a large ignition distance need not be newly repositioned relative to the tissue as frequently during the treatment of different sections of the tissue, because, with an instrument having a large ignition distance, the conditions for igniting a plasma exist at positions available within a large region of the instrument relative to the tissue. If the instrument is guided at a large distance over the tissue, a large-area tissue region can be simultaneously treated with the plasma. In addition, an increased distance of the distal end of the instrument from the tissue to be treated improves the view by the user of the instrument onto the tissue to be treated during the procedure, for example by means of an image transmission device on the distal end of an endoscope, to which or in which the instrument may be mounted.

In known instruments, their ignition distance from the tissue decreases noticeably with the use of the instrument in a dry environment compared with the use with in a moist or wet environment, which has the result that—for ignition—the instrument for must be moved closer to the tissue to be treated. As a result of this, the tissue surface (surface performance) to be treated with the instrument per unit of time may decrease due to the more frequently necessary repositioning of the instrument relative to the tissue. The requirement of time for a treatment is then correspondingly increased. Furthermore, the clear view onto the treatment region may be restricted due to the shadowing caused by the instrument. In addition, in the event of a close distance, there is an increased probability of contaminating the tip of the instrument with tissue.

From publication DE 10 2005 021 304 A1 an endoscopic surgical device for argon plasma coagulation has been known, said device comprising a working assembly that can be inserted into the endoscope and has a first channel in which an electrode is arranged and through which inert gas can be supplied to the tissue. The working assembly also has a second channel. It is disposed to supply-prior to the activation of the RF stream and during the actual APC-argon gas to the operating field in order to displace or keep flammable gases such as, e.g., oxygen or carbon monoxide, away from the operating field.

During the presentation "Challenges and solutions on the way to a deployable plasma endoscope" J. Winter et al. at the 6th International Conference on Plasma Medicine ICPM 6), Sep. 4-9, 2016, Bratislava, Slovakia, a device for endoscopic plasma therapy was introduced. An instrument is described that produces a core stream of helium and a shell stream of air. This is intended to avoid disadvantages during plasma generation caused by the accumulation of inert gas in a cavity.

It is the object of the present invention to state an instrument for the electrosurgical treatment of tissue at a large ignition distance.

SUMMARY

This object is achieved with an electrosurgical instrument as described herein.

The electrosurgical instrument according to the invention comprises a head with a lumen that can be filled with gas, in particular inert gas, e.g., argon, said lumen being associated with a channel. Furthermore, the head has at least one opening connected to the lumen, said lumen being disposed for the formation of a primary stream of gas (primary gas stream) in front of or next to the distal end of the instrument, outside the end of the instrument away from the distal end of the instrument, and has one or more second openings connected to the same lumen for the formation of a secondary stream of gas (secondary gas stream) next to the primary stream or, at least covering part of the periphery, around the primary stream. An electrode is arranged in the head. Preferably, the electrode is arranged in the head in such a manner that the gas for the primary stream flows past the electrode when the lumen is filled with gas. Preferably, the electrode is arranged in a channel section of the channel adjacent the first opening and terminating in the first opening.

If the lumen is filled with gas, in particular inert gas, for example argon, the gas flows through the lumen to the first opening, on the one hand, and to the second opening, on the other hand, and out of these openings. Thus the same gas flows out of the lumen through the openings. With the help of the electrode, it is possible to ignite a plasma for treating the tissue in front of the first opening.

The instrument is designed in such a manner that the secondary stream, preferably at least peripherally in sections, is formed around the primary stream, between the primary stream and a region of the environment of the instrument head. The region may contain, for example, humid gas, e.g., humid air or humid inert gas or mixtures thereof, aerosol and/or fluid. Accordingly, there will be a separation of the primary stream transversely with respect to the direction of flow of the primary stream from the region of the environment by the secondary stream that flows between the primary stream and the region of the environment. Preferably, the separation occurs at least peripherally in sections around the primary stream.

It is assumed that the formation of a secondary stream next to or—at least partially peripherally-around the primary stream leads to a stabilization of the primary stream by the secondary stream, on the one hand, and leads to the fact that contamination, moisture or fluid drops are carried away or blown away from the first opening by the secondary stream, on the other hand. In any case, the instrument according to the invention has a large ignition distance.

The instrument according to the invention is suitable for open surgical procedures, as well as for endoscopic procedures. In particular, in the latter case, there is an increased risk of adhesion of moisture or fluids to the distal end of the instrument and, as a rule, the risk of an environment that is moist, around the instrument head during use of the instrument.

As a result of the fact that the first opening and the second opening are supplied by the same lumen in the head of the instrument, it is not necessary two move two separate channels toward the instrument end. Rather, one gas line having a single channel that is not branched between the proximal end of the gas supply line on the gas supply device and the lumen can be used for supplying gas in the lumen. There results the possibility of designing a slim instrument, with a slim head that is particularly suitable for use with an endoscope when the instrument is fastened to an endoscope or guided in a working channel of an endoscope.

The instrument according to the invention can be developed further by one or more of the features described hereinafter or by one or more features depicted by the drawings.

It has been found to be advantageous if the second opening is arranged set back from the first opening. If the second opening is set back relative to the first opening, a distance for the formation of a secondary stream flowing outside the instrument head is provided between the second opening that is arranged set back and the first opening, said secondary stream flowing laterally next to the first opening past the first opening, and the moisture and droplets can thus be particularly effectively removed by the secondary stream from the region of the instrument head around the first opening.

The channel may have a primary stream channel section connected adjoining the opening, said primary stream channel section forming a subsection of the channel section in which the electrode is arranged. The primary stream section of the channel is arranged between the first opening and the lumen in order to connect the first opening to the lumen. If the instrument head is filled with gas, the gas exits from the lumen through the primary stream channel section and subsequently out of the first opening. In one embodiment, the cross-section of flow of the primary stream channel section may taper before the first opening in the direction toward the first opening. The cross-section of flow decreasing from before the first opening in the direction of the first opening results in an acceleration of the primary stream.

In the instrument head next to the primary stream channel section or at least peripherally in sections around the primary stream channel section, there is formed preferably at least one secondary stream channel section of the channel to which the second opening is connected in an adjoining manner in order to connect the second opening to the lumen. By means of the secondary stream channel section, it is possible to guide, orient and/or accelerate the gas stream flowing through the secondary stream channel section.

The inlet of the primary stream channel section connected to the lumen may be proximally set back relative to the second opening and/or in the direction counter the direction of flow through the primary stream channel section. As a result of this, one or more secondary stream channels sections may be formed next to the primary stream channel section or, at least partially peripherally, around the primary stream channel section. In addition, due to the set back location of the inlet, the location of separation of the gas stream flowing through the lumen is separated from the location of discharge from the second opening and the location of discharge from the first opening.

The inlet of the primary stream channel section may have a dividing edge that divides the gas stream into a primary stream through the primary stream channel section and a secondary stream through the second opening. The dividing edge may be knife-shaped, for example.

The first opening may be symmetrically round, in particular circular. The opening width of the first opening is preferably greater than the opening height of the first opening measured orthogonally relative to the opening width. The second openings are preferably arranged on the sides of the instrument head along the opening width of the first opening. For example, the first opening may be flattened or rounded. For example, the first opening may be oval. The first opening may be flattened up to the slit. Preferably, the first opening has a shape that will produce a fan-shaped primary stream.

The second opening preferably has the shape of a kidney, an arch, a sickle or a slit. Preferably, the second opening is arranged in such a manner that it may generate a secondary stream that surrounds the primary stream—at least along part of the periphery—that has, for example, the shape of a kidney, an arch or a sickle around the first opening and the primary stream channel section, respectively.

In the direction of flow, downstream of the second opening on the head of the instrument, there may be arranged a part projecting over the second opening, so that the secondary stream leaving the second opening flows between the projecting part and the primary stream. For example, the projecting part may be a section of the head or it may be a part mounted to the instrument, i.e., separate from the instrument. The projecting part prolongs a lateral expansion of the secondary stream exiting from the second opening and can thus contribute to a large ignition distance of the instrument.

Preferably, the instrument is disposed for forming a secondary stream next to or around the primary stream in such a manner that the secondary stream-measured on the first opening-displays a higher flow rate than the primary stream measured on the first opening. This can be accomplished, for example, by accelerating the secondary stream and/or by arranging elements reducing the flow rate of the gas for the primary stream on the inside of the head part.

The cross-section of flow of the secondary stream channel section upstream of the second opening may taper in the direction of the second opening. Due to the flow cross-sectional area of the secondary stream channel section decreasing in the direction of flow toward the second opening, the gas of the secondary stream flowing through the secondary stream channel section in the direction toward the second opening can be accelerated before being discharged from the second opening. For example for accelerating the secondary stream, the instrument may be disposed in such a manner that the secondary stream measured at the first opening displays a higher flow rate than the primary stream measured at the first opening.

As mentioned, the instrument is designed in such a manner that, when the lumen is filled with gas, fluid drops adhering to the first opening are blown away from the first opening by the secondary stream and/or taken up and carried away by the primary stream and/or by the secondary stream. This may be accomplished by an acceleration of the gas of the primary stream and/or the secondary stream before discharge through the first opening or through the second opening. Alternatively or additionally, the surface of the instrument head may preferably be hydrophobic at the first opening, for example due to a hydrophobic coating, so that the blowing away of fluid from the first opening by the secondary stream and/or the primary stream is improved even with lower volume flows of gas through the instrument head.

Preferably, the instrument head is configured for directing the secondary stream at the primary stream. To do so, the guide surfaces of the secondary stream channel section and/or the projecting part may be configured to form an acute angle between greater than 0° and smaller than 90°, with respect to the direction of flow of the primary stream.

The electrode may be arranged in the first opening, so that the end of the electrode at which the plasma is formed is in alignment with the first opening. Otherwise, the electrode may be arranged at the first opening in such a manner, for example, that the end is arranged proximally set back in the instrument head. The electrode may be arranged before the first opening, so that the gas-when the lumen is filled with gas-first flows out of the lumen past the end of the electrode before being discharged from the first opening. For example, the electrode may be arranged in the flow path of the gas that leads out of the lumen up to the first opening and out of the first opening in such a manner that the gas flows around the electrode on opposite sides of the electrode.

Preferably, the electrosurgical instrument comprises an electrode having the shape of a platelet, a spatula, a needle and/or a knife. Such designs impair the gas stream as little as possible. The electrode may be mounted in the instrument head, for example in the primary stream channel section, in that the electrode has a greater dimension in width compared with the channel of the instrument head, for example relative to the primary stream channel section, so that the electrode-upon the arrangement of the electrode in the channel-braces itself on opposite sides against the inner wall surface of the channel due to an elastic deformation of the electrode.

The end of the electrode, at which the plasma is formed when an RF power is applied to the electrode is preferably arranged downstream of the second opening in the direction of flow. In this manner, the probability of a spark breakdown from the end of the electrode through the second opening can be reduced. Preferably, the oppositely located end of the electrode facing away from the plasma viewed in the direction of flow is arranged after the second opening in order to minimize the probability of the a spark breakdown in front of the proximal end of the electrode through the second opening.

The electrosurgical instrument according to the invention is preferably a monopolar instrument. In such an instrument, the electric circuit from the RF generator to the electrode is closed via the plasma in the tissue of the patient by a neutral electrode attached to the patient and back into the RF generator. In contrast, a bipolar instrument comprises a feedback electrode, wherein the electric circuit of the electrode in the plasma and out of the plasma to the feedback electrode is closed.

In addition, a head for an electrosurgical instrument as described herein is disclosed. The instrument head may be a part that is separate from a gas supply line, which part can be connected to the gas supply line to produce the instrument.

BRIEF DESCRIPTION OF THE DRAWINGS

Further preferred features of the instrument according to the invention will be described with reference to the embodiments described hereinafter and illustrated with reference to the drawings, wherein their features may be interchangeably combined.

They show schematically and exemplarily.

DETAILED DESCRIPTION

Figure 1:
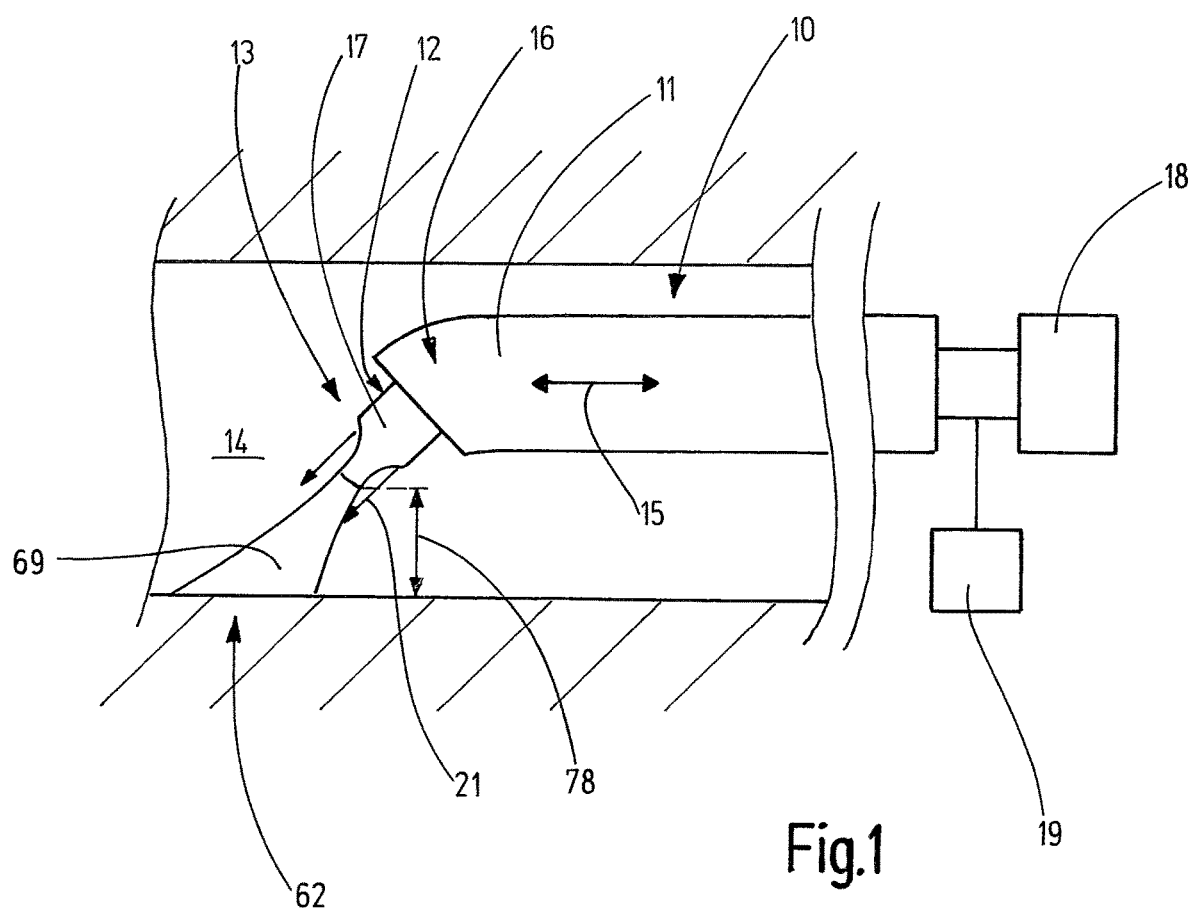
FIG. 1—a detail, partially in section, of an exemplary embodiment of a system according to the invention comprising an exemplary instrument according to the invention in a lumen of a human body, FIG. 2a—a detail, in longitudinal section, of a section of an exemplary embodiment of an instrument according to the invention, FIG. 2b—a front view of the instrument according to FIG. 2a, FIG. 2c—a detail, in longitudinal section, of the instrument according to FIG. 2a, with a guide part, FIG. 3a—a detail of an instrument according to the invention in another exemplary embodiment, FIG. 3b—a front view of the instrument according to the invention according to FIG. 3a, FIG. 4—another detail, in longitudinal section, of a section of the instrument according to the invention, FIG. 5—a longitudinal section of another exemplary embodiment of the instrument according to the invention, FIG. 6—a detail of an exemplary embodiment according to FIG. 5, FIG. 7a—a side view of an instrument head according to the invention, FIG. 7b—an instrument according to the invention with an instrument head according to FIG. 7a, FIGS. 8a, 8b, 8c—examples of electrode configurations in embodiments of the instrument according to the invention, FIGS. 9a, 9b—an exemplary embodiment of the instrument according to the invention, FIG. 10—an exemplary embodiment of the instrument head according to the invention, FIGS. 11, 12—exemplary arrangements of the second openings in exemplary embodiments of instruments according to the invention.

FIG. 1 shows, in a side view of the instrument 13, an inventive device 10 with an endoscope and a gas supply line 12 of an inventive electrosurgical instrument 13—said gas supply line extending through a working channel of the endoscope—in a cavity 14 of the body of a patient. Alternatively, the inventive instrument 13 may be guided, for example, outside on the endoscope 11. The endoscope 11 is shown in FIG. 1, as an example, with a distal end 16 that is curved with respect to the direction of longitudinal extent 15. The head 17 of the instrument 13 instrument head projecting from the working channel of the endoscope 11 forms a distal end section of the instrument 13. The instrument 13 is connected to a gas supply unit 18, which is also shown in FIG. 1, and to an RF generator 19.

Figure 2A:
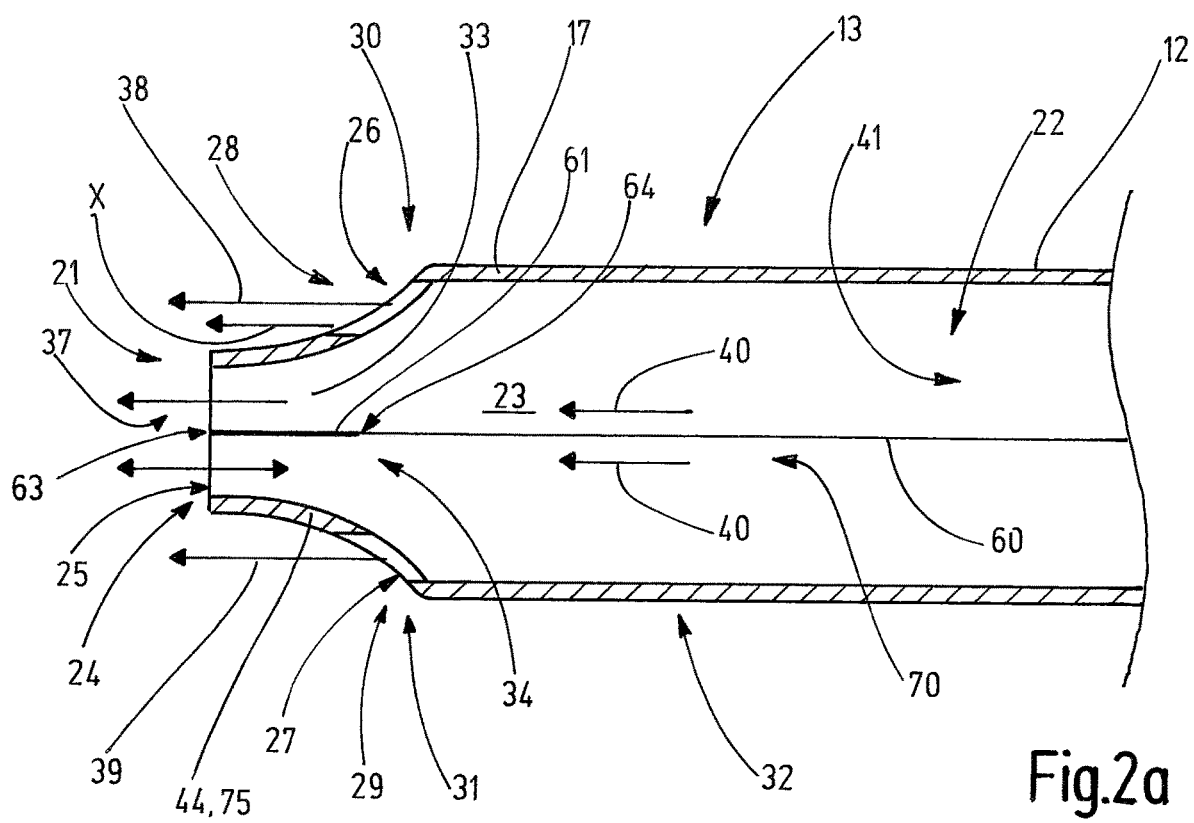
Figure 2B:
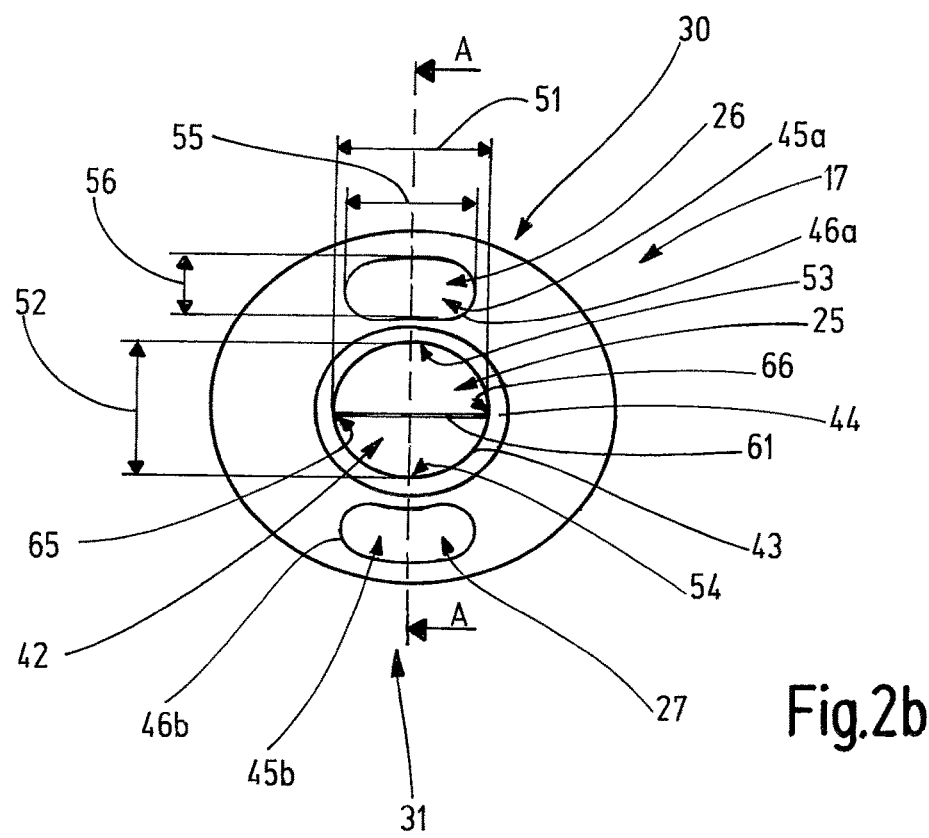

FIG. 2a shows a detail of the electrosurgical instrument 13 with its head 17 in a longitudinal sectional view (longitudinal sectional representation along intersection line A-A in FIG. 2b). FIG. 2b shows the instrument head 17 of FIG. 2a in a view from the front, from outside the instrument head 17 onto the face side 21 of the instrument head 17. The instrument 13 has a channel 22 that is connected to the gas supply line 18. The channel 22 is associated with a lumen 23 (cavity) in the instrument head 17 that is fluidically connected to a first opening 25 provided in a center region 24 of the face side 21 and to two second openings 26, 27 that are arranged in the peripheral regions 28, 29 of the face side 21 around the center region 24. In the depicted exemplary embodiment, the two openings 26, 27 are provided on opposite sides 30, 31 of the instrument head 17. While the first opening 25 and the second opening 26 in the exemplary embodiment depicted in FIGS. 2a and 2b are located in a face side 21 of the instrument head, the first opening 25 and the second openings 26, 27 may alternatively be provided on a lateral surface 32 of the instrument head 17.

Between the lumen 23 and the first opening 25, there is arranged a center primary stream channel section 33 of the instrument head 17, said section fluidically connecting the lumen 23 to the first opening 25.

Each of the second openings 26, 27 are arranged laterally on the inlet 34 in the primary stream channel section 33 on opposite sides of the inlet 34.

The second opening 26, 27 and the first opening 25 are arranged in such a manner that the secondary streams 38, 39 are formed on two opposing sides next to the primary stream 37 flowing out of the first opening 25.

If, as depicted, the second openings 26, 27 are arranged proximally set back from the first opening 25 counter the direction of flow 40 through the lumen 23, then—viewed in the direction of flow 40—a distance x is formed between the first opening 25, on one side, and the second openings 26, 27, on the other side. Due to the proximally set back second openings 26, 27, secondary streams 38, 39 of gas are formed next to the first opening 25, said secondary streams having traveled a flow path corresponding to the distance x from the second openings 26, 27. Preferably, the second openings 26, 27 are arranged-counter the direction of flow 40—relative to the first opening, each at the same distance x with respect to the first opening 25. For example, the distance x may be at most 5 millimeters, preferably at most 2 millimeters. In an exemplary embodiment, the distance x may be 1.2 millimeters, for example.

The direction of flow 40 is the direction in which the gas flows through the lumen 23 when gas is filled on the proximal end 41 into the instrument head 17, said gas flowing in the direction of flow 40 through the lumen 23 and to the first opening 25 and the second openings 26, 27.

The opening area 42 through which the gas moves out of the first opening 25 is bordered by an end edge 43 of the wall 44 of the channel 22 in the instrument head 17—here, an end edge 43 of the wall 44 of the primary stream channel section 33. The opening area 42 of the first opening 25 preferably extends in a direction perpendicular to the direction of flow 40 of the primary stream through the primary stream channel section 33. Each of the opening areas 45a, 45b of the second openings 26, 27 is bordered by an outer edge 46a, 46b of the cutout—this forming the opening 26, 27—in the wall 44 of the channel 22 through the instrument head 17. As shown, each of the opening areas 45a, 45b of the second openings 26, 27 is oriented inclined with respect to the direction of flow 40 to the first opening 25. The opening areas 45a, 45b of the second openings 26, 27 arranged on the periphery of the instrument head 17 face into the space outside the instrument head 17 on the face side 21 of the instrument 13.

As can be inferred from FIG. 2b, the first opening 25 of the exemplary embodiment has a flattened round shape in order to promote the formation of a primary stream 37 whose extent measured perpendicularly to the direction of flow of the primary stream 37 in a first dimension is greater than its extent perpendicular to the direction of flow of the primary stream 37 measured in a second dimension extending perpendicularly to the first dimension. To do so, the opening width 51 of the first opening 25 is greater than the opening height 52 measured perpendicularly thereto. Preferably, the first opening 25 has an oval form. Alternatively, the first opening 25 may be, for example, rectangular, circular or square. The first opening 25 may be flattened up to a slit for the formation of a slit nozzle to generate a fan-like gas stream. For example, the opening width 51 of the first opening 25 may have a dimension greater than zero and up to a maximum of 2.5 times the diameter of a tube that may represent the gas supply line 12. For example, the opening height 52 of the first opening 25 may greater than 0 millimeters and up to a maximum of 2.5 times the diameter of the tube. The opening width 51 of the first opening may be, for example between a minimum of 3 millimeters up to a maximum of 4 millimeters. The opening height 52 of the first opening 25 may be, for example, between a minimum of 0.7 millimeters to a maximum of 2 millimeters.

If an electrode with a planar cross-section is arranged in the head 17, the arrangement of the second openings 26, 27 is preferably symmetrical with respect to the area of the section. The second openings 26, 27 are preferably arranged symmetrically around the inlet 34 of the primary stream channel section 33. The second openings 26, 27 are preferably arranged, as illustrated, in such a manner that secondary streams 38, 39 will form, these flowing on opposite sides 53, 54 of the first opening 25, said sides 53, 54 extending along the opening width 51 of the first opening 25 (long sides 53, 54). If the second openings 26, 27 having, for example, the shape of a kidney, an arch, a sickle or a curved slit are arranged around the primary stream channel section 33—for example, its inlet 34—or the first opening 25 in such a manner that the second openings 26, 27 generate secondary streams 38, 39 which partially enclose the periphery of the primary stream 37 and which flow on the wall regions on opposite long sides 53, 54 of the first opening 25 past the long sides 53, 54 of the first opening 25, moisture and/or fluid can be blown off or away from the wall regions on the long sides 53, 54 of the first opening 25.

As illustrated, the opening width 55 of the second opening 26, 27 may be smaller than the opening width 51 of the first opening 25. For example, the opening width 55 of the second openings 26, 27 may each have a dimension greater than zero up to a maximum of 2.5 times the diameter of a tube that may form the gas supply line 12. For example, the opening height 56 of the second opening 26, 27 may each be a dimension greater than zero up to a maximum of 1.25 times the diameter of the tube. The opening width 55 of the second openings 26, 27, for example, may be between a minimum of 1.5 millimeters to a maximum of 3.5 millimeters. The opening height 56 of the openings 26, 27 measured perpendicularly with respect thereto may be, for example, between a minimum of 0.1 millimeters to a maximum of 0.5 millimeters.

The dimensions of the opening widths 55 of the second openings 26, 27 and/or the dimensions of the opening heights 56 of the second openings 26, 27 are preferably the same. The contents of the opening areas of the second openings 26, 27 are preferably the same. The opening area of the first opening 25 in the shown exemplary embodiment is smaller than the combined opening area of the second openings 26, 27. Alternatively, the opening area of the first opening 25 may be greater than the opening area of the combined opening areas of the second openings 26, 27, or the opening area of the first opening 25 may be the same as the combined opening areas of the second openings 26, 27.

Extending through the channel 22 and through the lumen 23, there is an electrical line 60 that is connected to an electrode 61 that is preferably mounted in the primary stream channel section 33. Die line 60 is connected to the RF generator 19 to generate a high-frequency alternate voltage in order to supply the electrode 61 continuously or in a pulsed manner with RF power and generate a plasma, e.g., an argon plasma, between the electrode 61 of the instrument 13 and the tissue 62. In the embodiments shown in the Figures, the instrument 13 comprises a single electrode 61. Alternatively, there may also be arranged more than one electrode 61 in the first opening 25 or inside the instrument head 17 in front of the first opening 25 (not illustrated). For example, at least two electrodes may be arranged in one channel section 33 adjacent to the first opening 25, and/or at least two first openings 25 may be arranged in the instrument head 17, in order to generate a combined primary stream 37, in which case at least one electrode 61 is arranged in the channel sections in front of the first openings 25.

The electrode 61 is preferably arranged so as to be centered and at least partially in the primary stream channel section 33. The distal end 63 of the electrode 61 may be flush, for example as illustrated, with the first opening 25 or, alternatively, project from the first opening 25 or be arranged inside the primary stream channel section 33.

The proximal end 64 of the electrode 61 may be arranged, for example as illustrated, inside the primary stream channel section 33, downstream of the inlet 34 in the primary stream channel section 33, so that the proximal end 64 of the electrode 61 is downstream of the inlet 34 in the primary stream channel section 33—viewed in the direction of flow 40. Alternatively, the proximal end 64 may be arranged between the two openings 26, 27 or in front of the second openings 26, 27, so that the second openings 26, 27—viewed in the direction of flow 40—are arranged downstream of the proximal end 64 of the electrode. The proximal end 64 of the electrode 61 may extend all the way into the lumen 23.

The electrode 61 is preferably arranged, as illustrated, in the primary stream channel section 33 so as to be oriented in such a manner that the electrode 61 extends, with its width measured from a lateral edge 65 of the electrode 61 to the opposite lateral edge 66, along the opening width 51 of the first opening 25. Preferably, as depicted, the electrode 61 is arranged in the instrument head 17 oriented in such a manner that the electrode 61 extends with its width along the lateral extent of the secondary streams 38, 39 defined by the opening width 55 of the second opening 26, 27.

Preferably, the electrode 61 has the shape of a platelet, a spatula, needle or knife. The electrode 61 may have a tapering distal end.

Preferably, the electrode 61 is fastened in the instrument head, in that a section—having the shape of a platelet, spatula or knife—of the electrode 61 is compared, based on an excess dimension of the section of the electrode 61, to an inside dimension of a section of the channel 22, for example the primary stream channel section 33 and/or the lumen 23, braces itself against opposing sides against the inside wall surface of the channel 22, for example the primary stream section 33 and/or the lumen 23. This is shown in an exemplary manner in FIGS. 8b and 8c, these showing partial sectional representations of the instrument head 17 along the intersection line C-C in FIG. 8a. FIG. 8b shows a platelet-shaped electrode 61 having a tapered distal end. FIG. 8c shows an electrode with a needle-shaped distal section and a platelet-shaped proximal section for mounting the electrode 61.

The path of flow from the lumen 23 to the lateral second openings 26, 27 is preferably free of electrodes in order to prevent turbulent gas streams.

The channel 22 is disposed to conduct the gas provided by the gas supply unit 18, for example inert gas, in particular argon, through the channel 22 into the lumen 23 of the channel 22 to the openings 25, 26, 27, where the gas flows out of the first opening 25 as the primary stream 37 and out of the second openings 26, 27 as peripheral secondary streams 38, 39 that flow next to and/or at least partially peripherally around the primary stream 37 away from the instrument head 17 in order to accompany the primary stream 37 through the secondary streams 38, 39 and/or at least envelop it at least partially in peripheral direction.

The cross section of the flow of the stream of the primary stream channel section 33 tapers in the direction toward the first opening 25. Inasmuch as the flow cross-sectional area content of the primary stream channel section 33 decreases accordingly in the direction of flow 40, there is—in the primary stream channel section 33—an acceleration of the gas flowing through the primary stream channel section 33 in the direction of the first opening 25 before the gas is discharged from the first opening 25.

The device 10 according to the invention works as follows:

For igniting the plasma 69 (FIG. 1), the user moves the instrument head 17 into the vicinity of the tissue 62 to be treated and activates the gas supply unit 18, so that gas will flow through the channel 22 in the direction of flow 40 from the inlet 70 into the lumen 23 in the head 17 into the lumen 23 of the instrument head 17. For example, the gas supply unit 18 may be disposed to supply the lumen 23 with a gas flow between at least 0.3 liters of gas per minute and at most with 5 liters of gas per minute, for example 1.5 liters of gas per minute. The supplied stream of gas flows in the direction of flow 40 through the lumen 23 and is subsequently divided in the instrument head 17 into a center primary stream 37 that is moved past the ignition electrode 61 and one or several secondary streams 38, 39 of gas, said streams flowing on opposite sides next to the primary stream 37, at least partially peripherally, away from the instrument head 17. The secondary streams 38, 39 and the primary stream 37 consist of the same gas because the first opening 25 and the second opening 26, 27 thereof are supplied in the lumen 23 arranged inside the instrument head 17.

In as much as the primary stream 37 is accelerated due to the tapering primary stream channel section 33, the static pressure in the primary stream 37 decreases. With the primary stream channel section 33 having converging walls forming a nozzle, it is possible to accelerate the gas for the primary stream 37 relative to the gas of the secondary streams 38, 39, so that—at the first opening 25—the primary stream 37 displays a higher flow rate than the secondary streams 38, 39 on the two opposite sides. Therefore, with the instrument 13 according to the invention, it is possible to achieve a two-stage velocity profile of the gas stream 37, 38, 39 away from the instrument head 17 with the use of only one working medium (gas). The velocity profile can be measured, for example, at the level of the first opening 25 on the first opening 25. Due to the pressure gradient, the secondary streams 38, 39 can be drawn toward the primary stream 37.

The secondary streams 38, 39 flow outside the channel wall 75 of the primary stream channel section 33 and outside past the first opening 25. Moisture or fluid that has collected on the edge of the first opening 25 is blown away or picked up by the primary stream 37 and the secondary stream 38, 39 that preferably grazes the region of the instrument head 17 around the first opening 25, in which case an aerosol can be formed, which aerosol will be carried away by the primary stream 37 and the secondary stream 38, 39, respectively. The removed moisture or fluid can thus no longer impair the ignition distance.

When the first opening 25 is arranged sufficiently close to the tissue 62, it is possible—by activation of the RF supply of the electrode 61 by the RF generator 19—for an ignition spark to form between the electrode 61 and the tissue 62 in the primary stream 37, said spark igniting the plasma. In doing so, the plasma forms mostly in the region of the primary stream 37 due to the ionization of the gas of the primary stream 37. Regions of the secondary streams 38, 39 on the primary stream 37 can also be ionized. Gas that flows farther outside can remain non-ionized despite the formed center plasma stream 37, so that—with the second openings 26, 27-a non-ionized flow of gas can be generated next to or at least partially peripherally around the plasma stream 37.

In order for plasma ignition to be successful, the first opening 25 on the face side 21 of the instrument head 17 must be moved at least up to an ignition distance 78 toward the tissue 62. As a rule, the ignition distance 78 is a few millimeters. A large ignition distance 78 is desirable because, with a small ignition distance 78, there is the increased risk that the instrument head 17 will be contaminated, for example by coming into contact with the tissue 62, on the one hand, and that the tissue region treated at the same time with the plasma 69 is relatively small, on the other hand.

It is assumed that, in the instrument 13 according to the invention, the expansion of the primary stream 37 in transverse direction and the mixing with the non-inert, moist surrounding medium after exiting from the first opening 25 on the instrument head 17 is reduced by the secondary stream 38, 39 flowing next to the primary stream 37 and thus enveloping the primary stream 37 preferably at least partially peripherally, as a result of which the working gas concentration of the primary stream 37 decreases less rapidly compared to an instrument 13 that does not provide a secondary stream 38, 39. It is also assumed that gas particles of the secondary stream 38, 39 from the second opening 26, 27 can move onto the primary stream 37. It is furthermore assumed that the formation of a primary stream 37 displaying a flow rate measured at the first opening 25, said flow rate being greater than the flow rate of the secondary stream also measured on the level of the first opening 25, leads to the stabilization of the primary stream 37 and thus to an enlargement of the ignition distance 77. In any event, the instrument 13 according to the invention displays a larger ignition distance 78, even in a moist environment as may exist, for example, in a cavity 14 of the body of a patient.

Figure 2C:
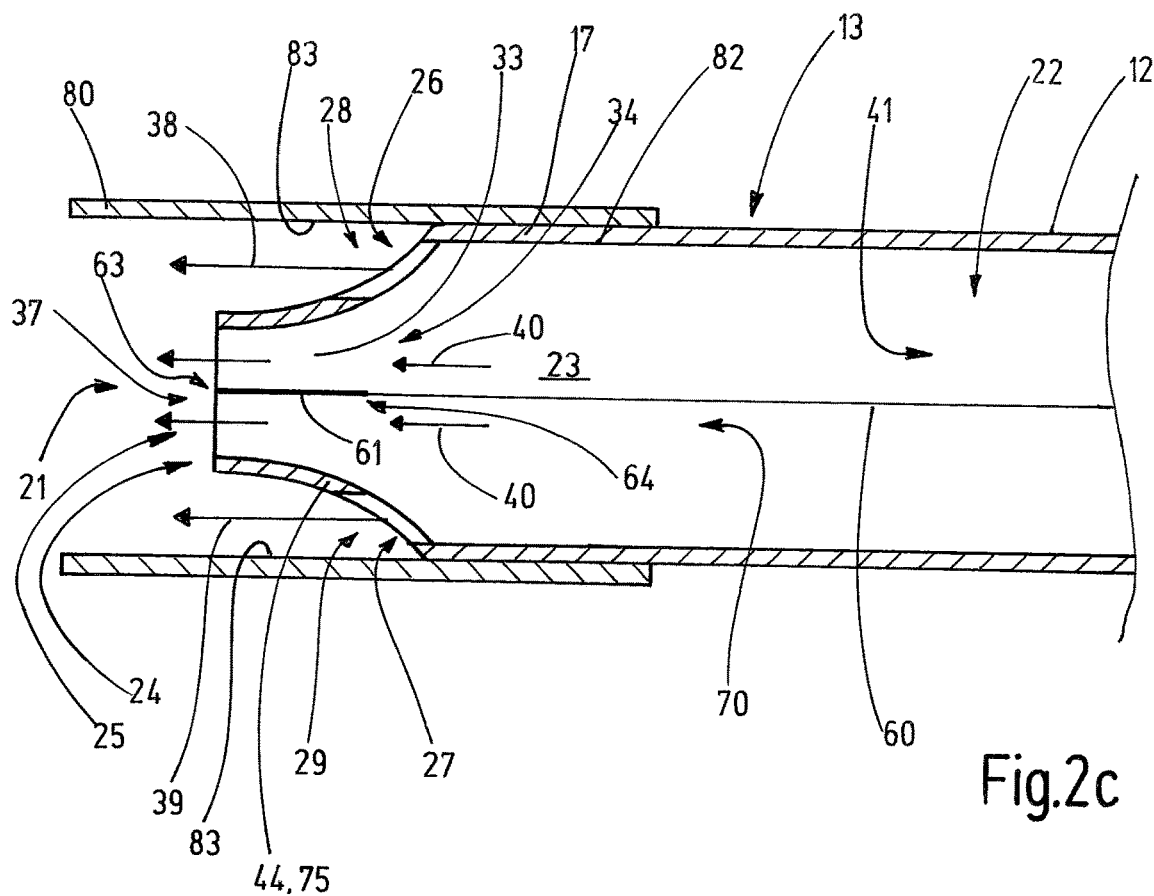

FIG. 2c shows the embodiment according to FIGS. 2a, 2b with a guide part 80 projecting preferably over the first opening 25, said guide part being configured as a tube element that is attached to the distal end 81 of the instrument head 17.

As an alternative or an addition to the tube-shaped guide part 80, respectively one, for example tongue-like, guide part 80 may be arranged on the second openings 26, 27 on the instrument head, said guide part 80 projecting beyond the second openings 26, 27 in the direction of flow of the secondary streams 38, 39 (not illustrated). The ends of the guide parts facing away from the probe head 17 may end in front of the first openings, so that the guide parts do not project beyond the first opening. The tongue-like guide parts 80 may be, for example, a projection of the wall 82 beyond the second openings 26, 27 that delimit the lumen 23 in outward direction.

The guide part 80 is designed and arranged to accomplish that the secondary gas streams 38, 39 flowing out of the second opening 26, 27 flow between the guide part 80 and the primary stream 37 and the primary stream channel section 33, respectively. The projecting guide part 80 delimits the secondary stream 38, 39 relative to the surrounding medium and is disposed to delay the expansion of the gas of the secondary stream 38, 39 toward the outside away from the primary stream 37 in order to contribute to an increase of the ignition distance 78. To do so, the guide part 80 has a radially inward facing guide wall surface 83, along which the secondary stream 38, 39 is flowing.

Figure 3A:
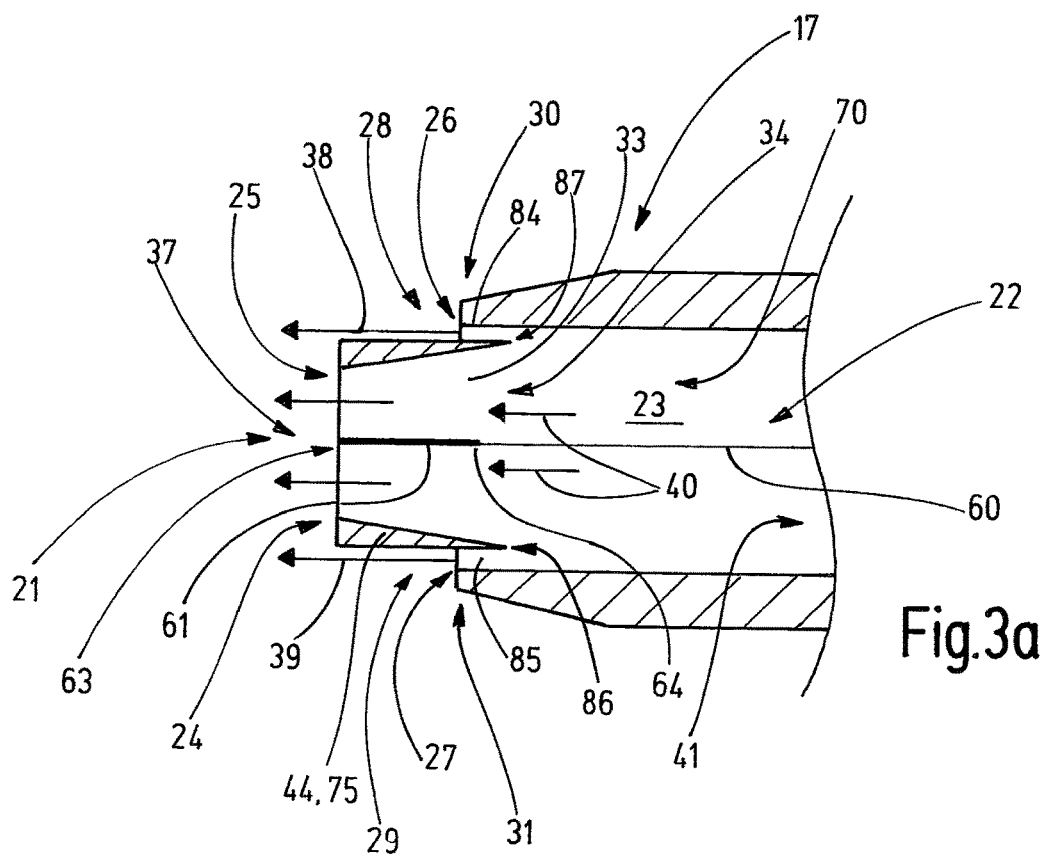
Figure 3B:
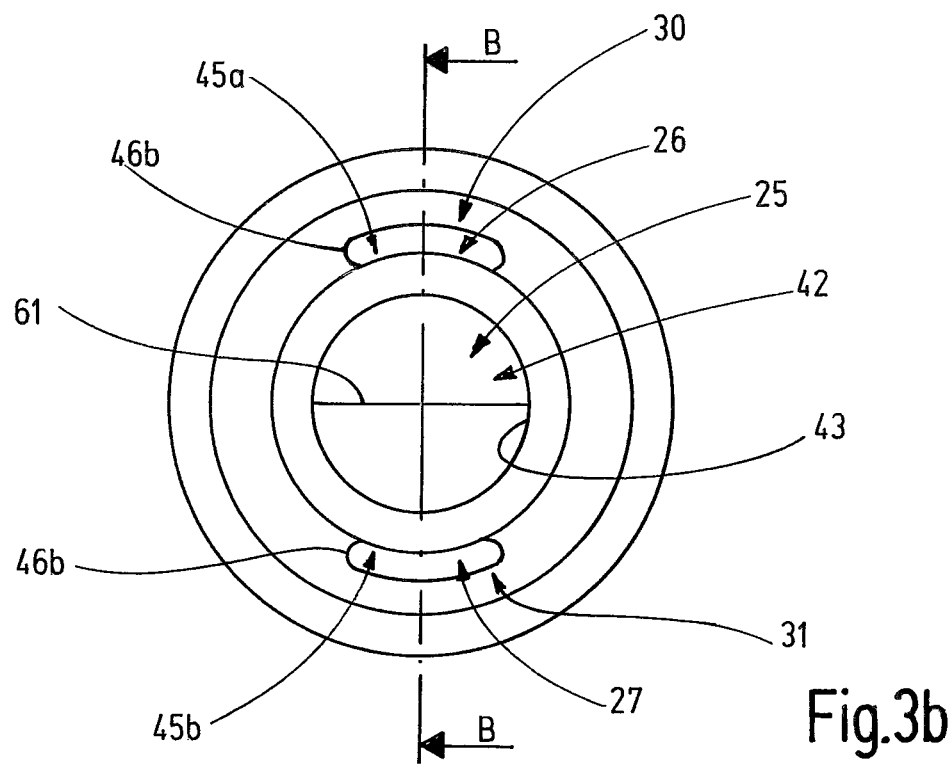

FIG. 3a is a view of a detail, in longitudinal section (longitudinal representation along the intersection line B-B in FIG. 3b) of a modified embodiment of the head 17 of the instrument 13 according to the invention. FIG. 3b shows a front view of the instrument of FIG. 3a. As can be seen in FIG. 3a, the inlet 34 of the primary stream channel section 33 arranged between the lumen 23 and the first opening 25 and connecting the lumen 23 to the first opening 25, is set back with respect to the second openings 26, 27 in the direction counter the direction of flow 40 of the gas through the lumen 23. Between the primary stream channel section 33 and the wall 82 of the instrument head 17, said wall having a wall section containing the lumen 23, there is formed, accordingly before each second opening 26, 27, respectively, one secondary stream channel section 83, 84 in the peripheral regions 28, 29 of the instrument head 17 next to the primary stream channel section 33. The secondary stream channel sections 84, 85 that are separated from each other, respectively border the corresponding second opening 26, 27. The secondary stream channel sections 84, 85 that are separate from each other each border the respective second opening 26, 27. For example, the secondary stream channel sections 84, 85 can have the cross-sectional form of a kidney, an arch or a sickle. The secondary stream channel sections 84, 85 are preferably free of electrodes. In particular, there are no electrodes arranged in the second openings 26, 27. The primary stream channel section 33 separates the gas flowing through the primary stream channel section 33, preferably in front of the inlet 34 of the primary stream channel section 33 up to the first opening 25, laterally from the gas that flows through the secondary gas stream channel sections 84, 85, and the medium outside the probe head 17, until the gas leaves through the first opening 25. The channel wall of the primary stream channels section 33 that delimits the primary stream channel section 33 is, accordingly, preferably free of openings between the inlet 34 of the primary stream channel 33 up to the first opening 25. Alternatively or additionally, it preferably applies to both secondary stream channel sections 84, 85 that the channel wall of the secondary stream channel section 84, 85 delimiting the secondary stream channel section 84, 85 is preferably free of openings between the inlet in the secondary stream channel section 84, 85 up to the second opening 26, 27 in order to laterally separate the gas flowing through the secondary stream channel sections 84, 85.

Therefore, the instrument head 17 is configured so as to divide the gas flowing through the lumen 23 inside the instrument head 17 into at least one center primary stream 37 through the primary stream channel section 33 and into two peripheral secondary streams 38, 39 through the oppositely located longitudinal sides of the primary stream channel section 33 in the instrument head 17 in the secondary stream channel sections 84, 85. The secondary stream channel sections 84, 85 are provided next to the primary stream channel section 33 and, as depicted, surround the primary stream channel section 33 at least peripherally in sections.

Accordingly, the instrument head 17 is configured in such a manner that the location of division of the gas stream into the primary stream 37 and the secondary streams 38, 39 is set back relative to the second opening 26, 27, counter the direction of flow 40.

The division of the stream through the lumen 23 is accomplished on a dividing edge 86 inside the instrument head 17 on the inlet 34 of the primary stream channel section 33, said edge being preferably configured so as to taper knife-like, counter the direction of flow 40.

The secondary stream channel sections 84, 85 are disposed to guide the secondary stream 38, 39 before being discharged from the second opening 26, 27. Referring to the exemplary embodiment shown in FIG. 3*a*, the cross-sections of flow of the secondary stream channel sections 84, 85 remain constant from the location of division up to the individual second opening 26, 27. For example, each secondary stream channel section 84, 85 may have a length greater than 0 millimeters up to a maximum of 30 millimeters, in particular greater than 0 millimeters up to a maximum of 10 millimeters, preferably greater than 0 millimeters up to a maximum of 5 millimeters.

The dividing edge 86 may be arranged on a dividing projection extending counter the direction of flow 40 into the channel 22 (not illustrated), said projection being arranged, additionally or alternatively to the primary stream channel section 33 and/or the secondary stream channel section 84, 85 in the instrument head 17. The dividing projection is arranged between the primary stream 37 and the secondary stream 38, 39 inside the instrument head 17. The described dividing edge 86 may be provided on the dividing projection.

In the exemplary embodiment according to FIGS. 3*a*, 3*b*, the primary stream channel section 33 is configured as in the exemplary embodiment according to FIGS. 3*a*, 3*b* in such a manner that the cross-sectional area of flow of the primary stream channel section 33 decreases in the direction of flow 40 out of the lumen 23 toward the first opening 25, so that the gas in the primary stream channels section 33 is accelerated.

As is obvious from FIG. 3*b*, the second openings 26, 27 and the secondary stream channel sections 84, 85 enclose the primary stream channel section 33—partially peripherally, in an arcuate manner. In the exemplary embodiment according to FIGS. 3*a* and 3*b*, the first opening 25 is circular. The contours delimiting the second openings 26, 27 have a circular arc profile. Deviating therefrom, the first opening 25 may, for example, have a flattened polygonal or flattened rounded, e.g. oval, form. The second openings 26, 27 and the secondary stream channel sections 84, 85 each may have a form (in cross-section) deviating from the circular arc profile in order to enclose the primary stream channel section 33 partially peripherally. The opening areas 45*a*, 45*b* of the second openings 26, 27 are planar and are each delimited by an end edge 46 of the secondary stream channel section 84, 85. In the exemplary embodiment according to FIG. 3*a*, the opening areas 45*a*, 45*b* of the second openings 26, 27 essentially face in the same direction away from the instrument head 17 as does the opening surface 42 of the first opening 25. Other than that, the description relating to the embodiment according to FIGS. 1, 2*a* and 2*b* applies analogously to the embodiment according to FIGS. 3*a*, 3*b*.

Preferably, the instrument head 17 is configured in such a manner that it generates one or more secondary streams 38, 39 next to the primary stream 37 or around the primary stream 37, wherein the secondary stream or secondary streams 38, 39 measured at the first opening 25 display a higher flow rate or flow rates than the primary stream 37 measured at the first opening 25. To accomplish this, the instrument head 17 may, for example, be disposed for accelerating the gas for the secondary gas stream or streams 38, 39 and/or for reducing the velocity of the gas for the primary stream 37. In order to reduce the velocity of the gas for the primary stream, it is possible, for example, to arrange elements such as screens and/or one or more blades on the inside of the instrument 17 in the flow path of the gas for the primary stream. With the aid of the instrument head 17, it is possible to achieve a two-stage velocity profile of the gas stream 37, 38, 39, away from the instrument head 17, by employing only one working medium (gas). As a result of this, a pressure gradient may exist between the primary stream 37 and the secondary stream or streams 38, 39, as a result of which the primary stream 37 can be drawn to the secondary stream 38 or the secondary streams 39.

Figure 4:
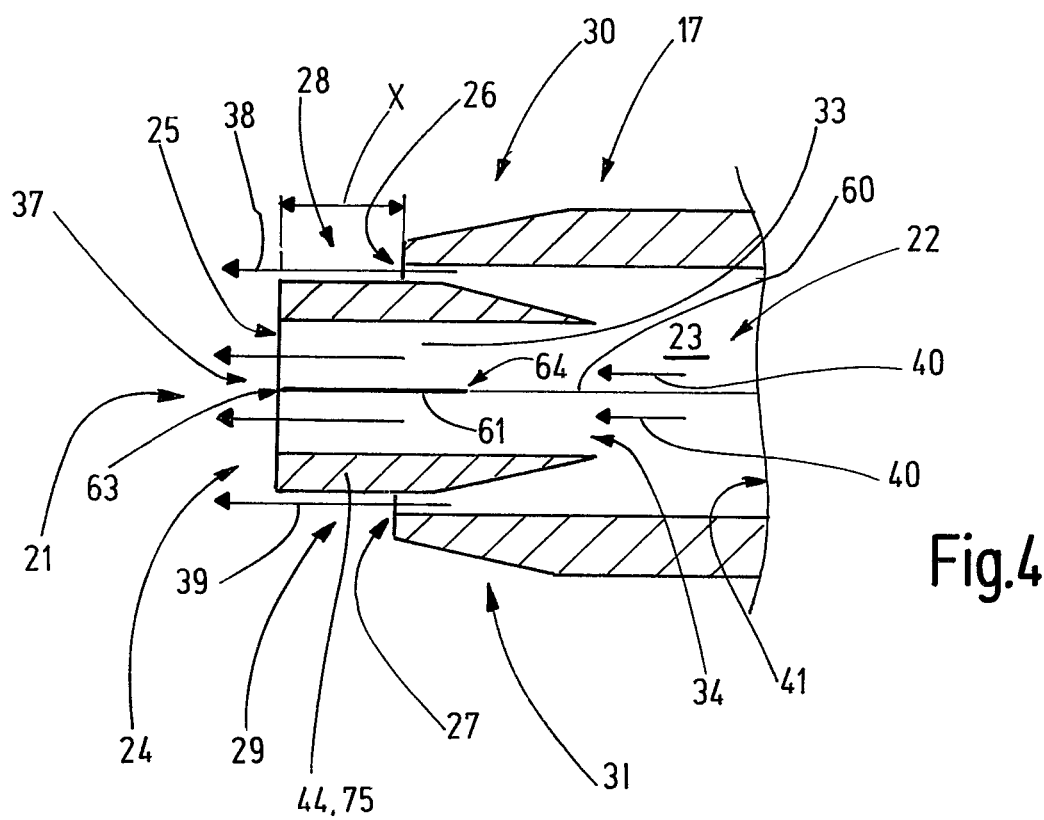

FIG. 4 shows a detail of an exemplary embodiment of the instrument 13 according to the invention having the instrument head 17, wherein the flow cross-sectional areas of the secondary stream channel sections 84, 85—in modification of the exemplarity embodiment according to FIG. 3*a*—decrease in front of the inlet 87 of the secondary stream channel section 84, 85 in the direction of flow 40 toward the second opening 26, 27. As a result of this, the gas flowing from the lumen 23 through the secondary stream channel section 84, 85 to the second opening 26, 27 is accelerated in the secondary stream channel section 84, 85. In the illustrated embodiment, the flow cross-section of the primary stream channel section 33 remains constant from the inlet 34 of the primary stream channel section 33 to the first opening 25. A modification is possible, wherein the flow cross-sectional area of the primary stream channel section 33, as well as the flow cross-sectional areas of the secondary stream channel sections 84, 85, decrease in the direction toward the openings 25, 26 in order to accelerate the gas before it passes through the first opening 25 and the second openings 26, 27, respectively. For example, the instrument head 17 can be configured for the acceleration of the gas in the secondary stream channel sections 84, 85 in such a manner that the flow rates of the secondary streams 38, 39 at the first opening are higher than the flow rate of the primary stream 37 at the first opening.

Other than that, the description of FIG. 4 applies analogously to FIG. 3*a*. An exemplary view of the embodiment according to FIG. 4 from the front is shown by FIG. 3*b*.

Figure 5:
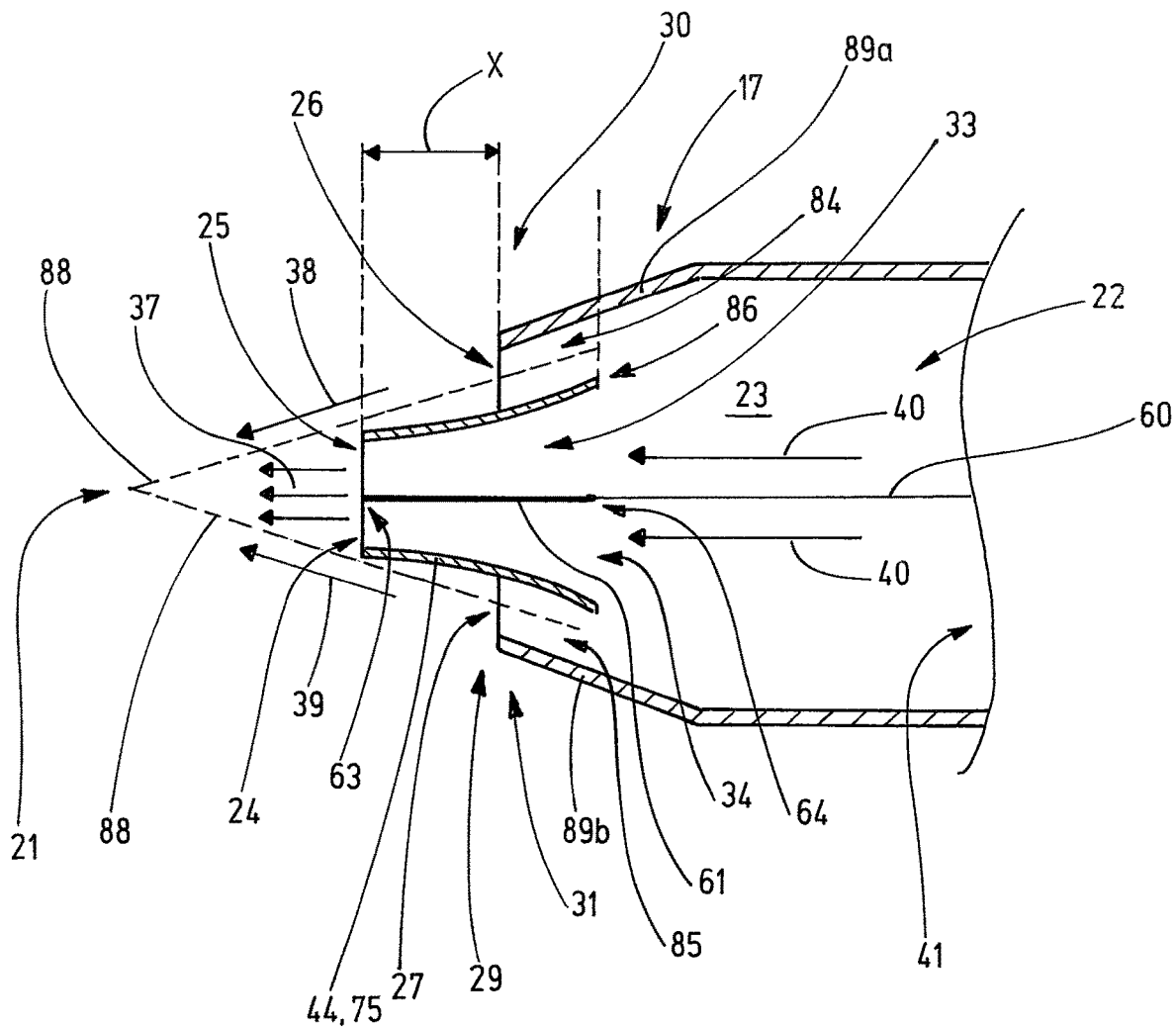

FIG. 5 shows a longitudinal sectional view of a detail of the instrument 13 according to the invention with an instrument head 17 according to a modified embodiment. In this embodiment, the secondary stream channel sections 84, 85 are configured in such a manner that they direct the secondary streams on both sides of the primary stream at the primary stream in the primary stream channel section 33 and/or outside the primary stream channel section 33 downstream of the first opening 25, as is indicated by the dashed lines 88 that indicate the directions of flow of the secondary streams 38 out of the two openings 26, 27. The directions of flow result from the arrangement of the wall surfaces of the secondary stream channel sections 84, 85 that delimit the secondary stream channel sections 84, 85. The secondary stream channel sections 84, 85 can be arranged oriented in such a manner that the secondary streams 38, 39 are aligned on the opening edge of the first opening 25. Thus, it can be achieved that a large amount of gas of the secondary streams 38, 39 grazes the opening edge of the first opening.

In the embodiment according to FIG. 5, the wall sections 89a, 89b of the instrument head 17 delimiting the lumen 23 converge in such a manner that the flow cross-sectional area of the lumen 23 decreases in the direction toward the openings 25, 26, 27. Due to the decrease of the flow cross-section of the lumen 23 in the direction toward the openings 25, 26, 27, the gas flowing through the lumen 23 is accelerated already before its division into primary stream 37 and secondary stream 38, 39.

Other than that, the description of the embodiment applies analogously to FIGS. 3a, 3b.

Figure 6:
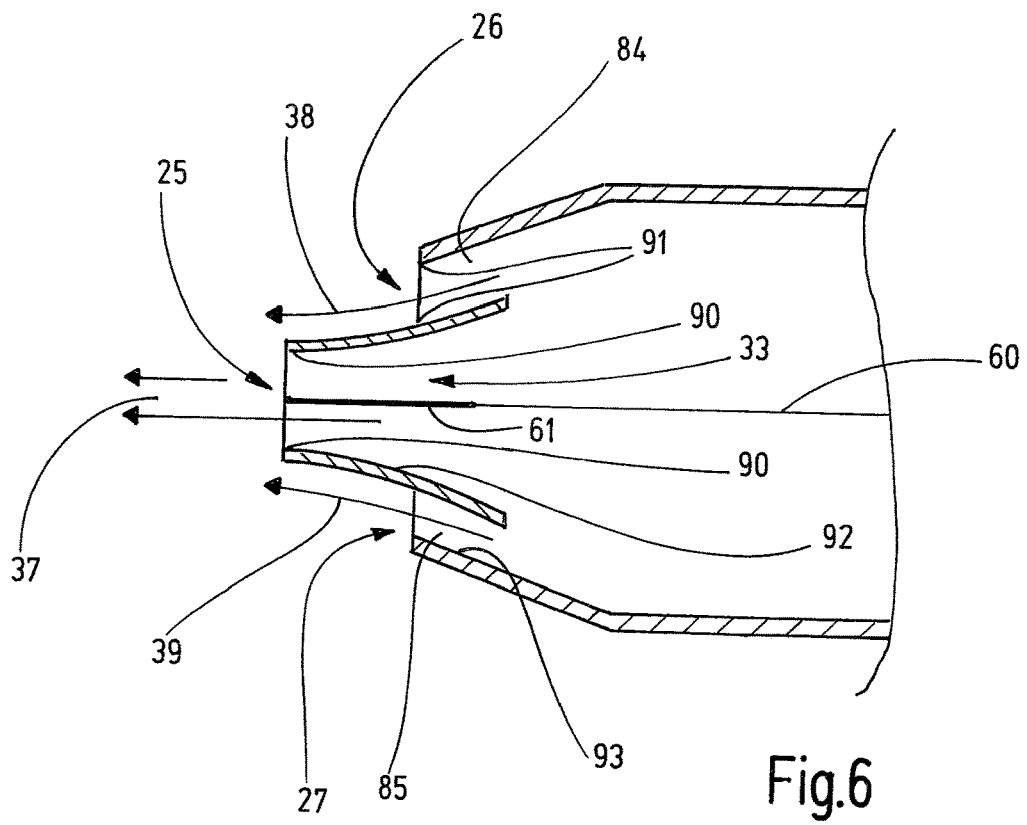

FIG. 6 shows a detail of an instrument 13 corresponding to the embodiment according to FIG. 5, said instrument having hydrophobic wall surfaces. The wall surfaces of the embodiments of FIGS. 1 to 4 may have corresponding hydrophobic wall surfaces:

It is of advantage for blowing or carrying away water-containing fluid from the first opening 25 and/or from the second opening 26, 27 by means of the secondary streams 38, 39, and/or the primary stream 37, if the surface of the instrument head 17 on the first opening 25 and/or on the second openings 26, 27 is hydrophobic. If the wall surface 90 delimiting the first opening 25 inward and/or the wall surfaces 91 delimiting the second openings 26, 27 inward are hydrophobic, the risk that moisture or fluid will collect in the first opening 25 and in the second openings 26, 27, respectively, and plug them is minimized.

Preferably, the wall surfaces 92, 93 bordering the primary stream channel section 33 and/or bordering the secondary stream channel sections 84, 85 inward are hydrophobic in order to minimize the risk that moisture will collect in the primary stream channel section 33 and in the secondary stream channel sections 84, 85 and plug them.

The wall surfaces 90-93 may be made hydrophobic by a hydrophobic coating, for example. Hydrophobic wall surfaces 90-93 may be made of PTFE or may be PTFE-coated. The probe head 17 is preferably made of ceramic with a hydrophobic surface.

Figure 7A:
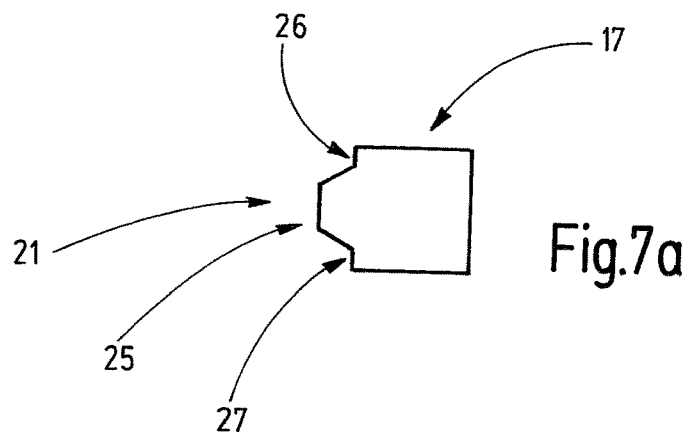
Figure 7B:
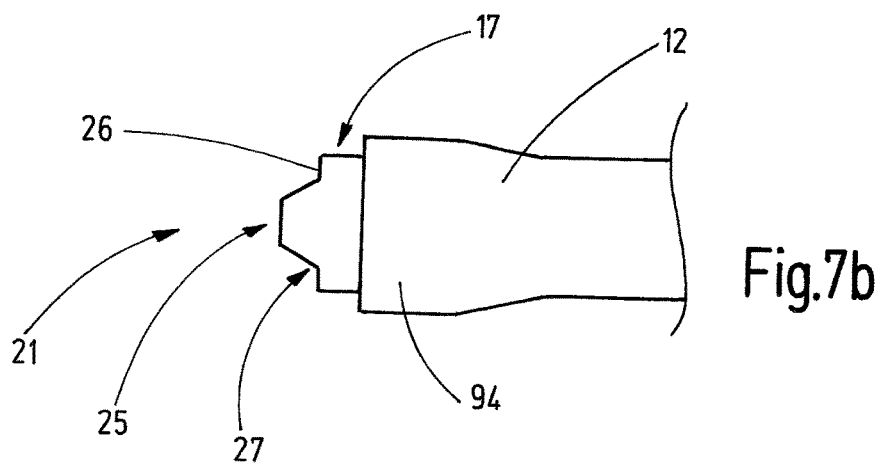

FIG. 7a shows the profile of an instrument head 17 according to the invention, for example made of ceramic, said instrument head being a part separate from the gas supply line 12 that connects the instrument head 17 for the supply of gas to a gas supply unit 18. FIG. 7b shows an instrument head 17 according to FIG. 7a, said instrument head being connected to a gas supply line 12—for example a tube or also flexible pipe—of the instrument 13, in which case, according to the example, the instrument head 17 is held in a distal end 94 of the supply line 12.

As an alternative to an instrument head 17 as the part that is separate from the gas supply line 12, the instrument head 17 may be a section on the distal end 94 of a gas supply line 12. For example, an instrument head 17 according to the invention can be produced, in that the sheath of a line 12, for example a tube or a flexible pipe, is notched on its end on opposite sides transversely with respect to the direction of longitudinal extent of the line 12 radially up to the lumen that is delimited by the sheath, and in that the section 12 at the end of the line 12 is flattened by compression between the notches, on one side, and the end of the line 12, on the other side. In so doing, the second openings 26, 27 open on the notches. The opening at the end of the line forms the first opening 25 in which an electrode can be inserted. The design of the instrument head 17, e.g., according to FIGS. 7a, 7b may be equal to this described design, however the head 17 may consist of ceramic.

FIG. 9b is a longitudinal section through an instrument head 17 according to the invention (along section line C-C of FIG. 9a: electrode 61 and supply line 60 are not shown). Depicted are the flow cross-sectional areas $A_i$ of the primary stream channel section 33 at its narrowest point, as well as the flow cross-sectional areas AA of the secondary stream channel sections 84, 85 at their narrowest points. The ratio of the sum of the flow cross-sectional areas $A_i$ of the primary stream channel sections 33 at their narrowest points with respect to the sum of the flow cross-sectional areas AA of the secondary stream channel sections 84, 85 at their narrowest points is preferably a maximum of 3 to 1 to a minimum of 1 to 3. Preferably, the sum of the flow cross-sectional areas $A_i$ of the first primary stream channel sections 33 at their narrowest points is greater than the sum of the flow cross-sectional areas AA of the secondary stream channel sections 84, 85 at their narrowest points. The secondary stream channel sections 84, 85 and/or the primary stream channel sections 33 can be configured in such a manner that the gas flowing in the channel sections reaches the speed of sound.

Figure 10:
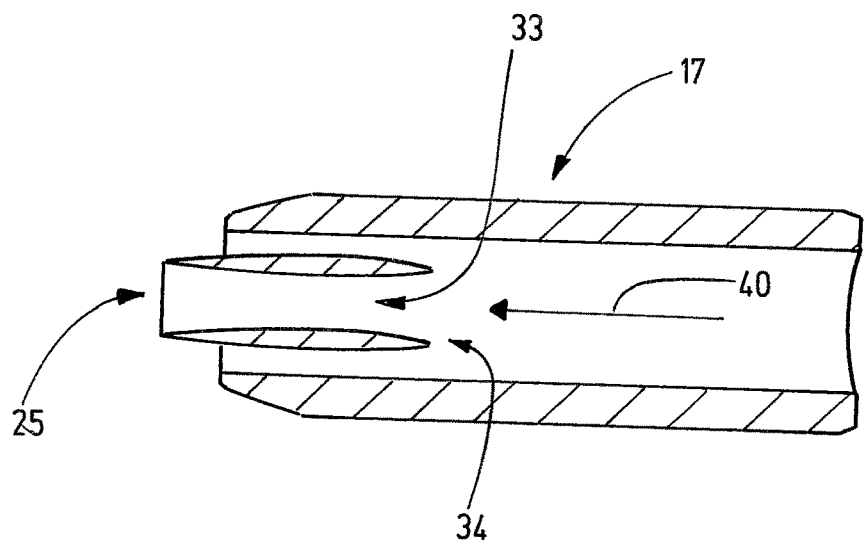

FIG. 10 shows an embodiment of an instrument head 17 of the inventive instrument 13, in longitudinal section (the electrode 61 and its supply line 60 are not shown). The wall of the primary stream channel section 33 is, as shown, configured in such a manner that the two intersection areas resulting in the event of the longitudinal section (longitudinal section along the direction of flow 40 in the center through the instrument head 17) of the wall of the primary stream channel section 33 have the shape of a drop. The primary stream channel section 33 is configured in such a manner that the dimension measured transversely with respect to the direction of flow of each longitudinal intersection area initially increases from the rounded proximal end (at the inlet 34) of the primary stream channel section 33 in the direction of the first opening 25 and then decreases in a tapered manner downstream in such a manner that the longitudinal section tapers in the direction toward the distal end of the primary stream channel section 33. If the primary stream channel section 33 of an instrument head 17 according to the invention is configured in such a manner that the dimension of the longitudinal intersection area measured transversely with respect to the direction of flow 40 decreases toward the distal end of the primary stream channel section 33 in such a manner that the longitudinal section tapers, moisture can be blown away from the first opening 25 in a particularly effective manner.

Figure 11:
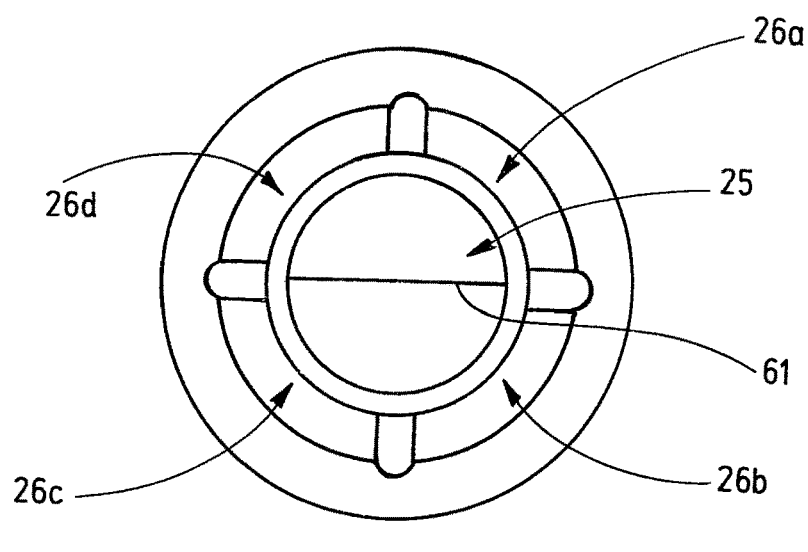
Figure 12:
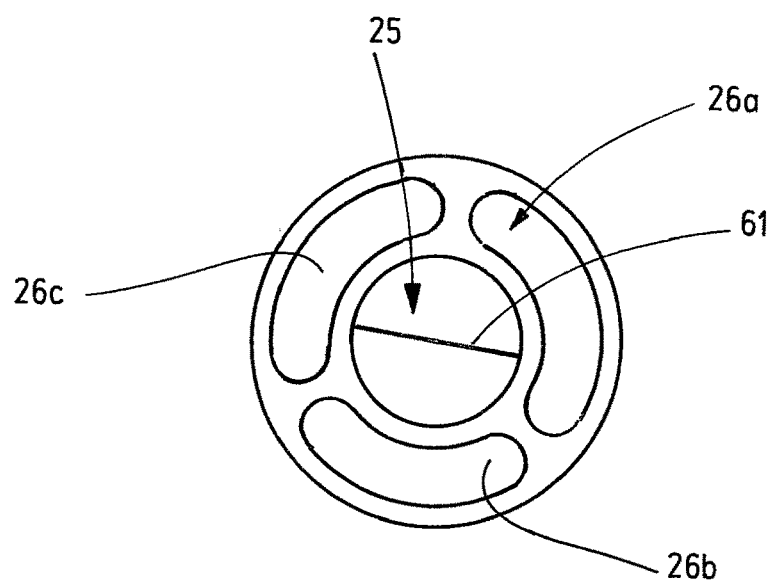

FIG. 11 and FIG. 12 show embodiments of the instrument head 17 from the front with several second openings 26a-26d and 26a-26c, respectively, arranged on a periphery around the primary stream channel section 33. The arrangement of the second openings of the instrument head 17 according to the invention may be symmetrical with respect to the plane that extends along the width of the electrode and its length. FIG. 12 shows an alternative thereto, wherein the arrangement of the second openings 26a-26c is not symmetrical with respect to the electrode plane.

Described is a new instrument 13 for electrosurgical treatment. The instrument 13 comprises an instrument head 17. The instrument head 17 forms a conveying body with a lumen 23 that can be filled with gas. The lumen 23 is connected to at least one first opening 25 and at least one second opening 26, 27 in the instrument head 17, from which openings the gas leaves out of the instrument head 17 when the lumen 23 is filled with gas. A primary stream 37 of gas leaves through the first opening 25 out of the instrument head 17 in the direction toward the tissue 62. The second opening 26, 27 is arranged relative to the first opening 25 in such a manner that a secondary stream 38, 39 leaves out of the second opening 26, 27, which secondary stream flows next to the primary stream 37 and/or—optionally with additional secondary streams 38, 39 out of additional second openings 26, 27—away from the instrument head 17, at least partially peripherally surrounding the primary stream 37. The secondary stream 38, 39 preferably envelops the primary stream 37. In the path of flow of the gas from the inside of the instrument head 17 out of the first opening 25, there is arranged an electrode 61 for igniting a plasma between the first opening 25 and the tissue 62 to be treated. Due to the secondary stream 38, 39 disposed so as to accompany the primary stream 37, an ignition of the plasma is successful even if the instrument 13 is at a relative large distance 78 from the tissue 62 to be treated. If the primary stream 37 is formed with the instrument according to the invention as a core stream out of the first opening 25 and the secondary stream 38, 39 is formed as an enveloping stream out of the second openings 26, 27, an ignition of the plasma is already successful at relatively large distances of the instrument 13 from the tissue 62. The core stream 37 and the enveloping stream 38, 39 are fed by the same lumen 23, so that said streams consist of the same gas.

LIST OF REFERENCE SIGNS

| 10 | Device |
|---|---|
| 11 | Endoscope |
| 12 | Gas supply line |
| 13 | Instrument |
| 14 | Cavity (lumen) of the body |
| 15 | Direction of longitudinal extent |
| 16 | Distal end of the endoscope |
| 17 | Head |
| 18 | Gas supply unit |
| 19 | RF generator |
| 21 | Face side |
| 22 | Channel |
| 23 | Lumen |
| 24 | Center region |
| 25 | First opening |
| 26, 26a 26d | Second opening |
| 27 | Second opening |
| 28 | Peripheral region |
| 29 | Peripheral region |
| 30 | Side of the instrument head |
| 31 | Side of the instrument head |
| 32 | Lateral surface |
| 33 | Primary stream channel section |
| 34 | Inlet |
| 37 | Primary stream/plasma flow |
| 38 | Secondary stream |
| 39 | Secondary stream |
| 40 | Direction of flow |
| 41 | Proximal end |
| 42 | Opening area |
| 43 | End edge |
| 44 | Wall |
| 45a, 45b | Opening areas |
| 46a, b | Edge |
| 51 | Opening width |
| 52 | Opening height |
| 53 | Side |
| 54 | Side |
| 55 | Opening width |
| 56 | Opening height |
| 60 | Electrical line |
| 61 | Electrode |
| 62 | Tissue |
| 63 | Distal end of the electrode |
| 64 | Proximal end of the electrode |
| 65 | Edge |
| 66 | Edge |
| 69 | Plasma |
| 70 | Inlet |
| 75 | Channel wall |
| 78 | Distance/ignition distance |
| 80 | Guide part |
| 81 | Distal end |
| 82 | Wall |
| 82a, 82b | Wall section |
| 83 | Guide wall surface |
| 84 | Secondary stream channel section |
| 85 | Secondary stream channel section |
| 86 | Dividing edge |
| 87 | Inlet |
| 88 | Lines |
| 89a, b | Wall sections |
| 90-93 | Wall surfaces |
| 94 | Distal end of the gas supply line |
| x | Distance |
| $A_i$ | Flow cross-sectional area |
| $A_A$ | Flow cross-sectional area |
| A-A | Intersection line |
| B-B | Intersection line |
| C-C | Intersection line |

The invention claimed is:

1. An electrosurgical instrument comprising:
a distal head having an exterior surface extending about a longitudinally extending channel defining a single gas-fillable lumen therein;
a first exterior opening in the exterior surface at a distal end of the head in direct communication with a space outside of the head and in fluidic communication with the single gas-fillable lumen such that a portion of a gas supplied from the single gas-fillable lumen forms a primary stream of gas directed longitudinally away from the distal end of the head; and
at least one second exterior opening in the exterior surface at the distal end of the head in direct communication with the space outside of the head and in fluidic communication with the single gas-fillable lumen such that another portion of the gas supplied from the single gas-fillable lumen forms a secondary stream of gas directed longitudinally away from the distal end of the head along the primary stream or at least partially peripherally around the primary stream;
wherein an electrode is arranged in or adjacent to the first exterior opening in the distal end of the head for forming a plasma stream from the primary stream of gas; and
wherein the head is free of an electrode in the at least one second exterior opening and is free of an electrode adjacent to the at least one second exterior opening for forming a non-ionized stream of gas from the secondary stream such that the head is adapted to discharge the plasma stream and the non-ionized stream of gas into the space outside of the head with the non-ionized stream of gas along or at least partially peripherally around the plasma stream.

2. The electrosurgical instrument according to claim 1, wherein the at least one second exterior opening is set back from the first exterior opening.

3. The electrosurgical instrument according to claim 1, wherein the channel has a primary stream channel section that is connected to the first exterior opening, and wherein a flow cross-section of the primary stream channel section decreases before the first exterior opening in a direction toward the first exterior opening.

4. The electrosurgical instrument according to claim 1, wherein the channel has a primary stream channel section that is connected to the first exterior opening, wherein an inlet of the primary stream channel section ends flush with the at least one second exterior opening, or wherein the inlet of the primary stream channel section is arranged so as to be proximally set back from the at least one second exterior opening.

5. The electrosurgical instrument according to claim 1, wherein an opening area of the first exterior opening is larger than an opening area of the at least one second exterior opening.

6. The electrosurgical instrument according to claim 1, wherein an opening width of the first exterior opening is greater than an opening height of the first exterior opening, measured orthogonally relative to the opening width.

7. The electrosurgical instrument according to claim 1, wherein the at least one second exterior opening has the shape of a kidney, an arch, or a sickle.

8. The electrosurgical instrument according to claim 1, wherein the channel has a primary stream channel section that is connected to the first exterior opening and a secondary stream channel section that is connected to the at least one second exterior opening, wherein the secondary stream channel section is arranged either next to the primary stream channel section or surrounding the primary stream channel section.

9. The electrosurgical instrument according to claim 8, wherein a flow cross-section of the secondary stream channel section decreases before the at least one second exterior opening in a direction toward the at least one second exterior opening.

10. The electrosurgical instrument according to claim 1, wherein the channel has a primary stream channel section that is connected to the first exterior opening and a secondary stream channel section that is connected to the at least one second exterior opening, and an inlet of the primary stream channel section includes a dividing edge between the primary stream channel section and the secondary stream channel section that divides the gas supplied from the single gas-fillable lumen into the primary stream and the secondary stream.

11. The electrosurgical instrument according to claim 1, wherein the electrosurgical instrument is a monopolar instrument.

12. The electrosurgical instrument according to claim 1, wherein a distal end of the electrode is arranged downstream of the at least one second exterior opening, viewed in a gas flow direction.

13. The electrosurgical instrument according to claim 1, wherein the electrode has the shape of a platelet, a spatula, a needle or a knife.

14. An electrosurgical head for an electrosurgical instrument comprising:
an exterior surface extending about a longitudinally extending channel defining a single gas-fillable lumen therein;
a first exterior opening in the exterior surface at a distal end of the electrosurgical head in direct communication with a space outside of the head and in fluidic communication with the single gas-fillable lumen such that a portion of a gas supplied from the single gas-fillable lumen forms a primary stream of gas directed longitudinally away from the first exterior opening;
at least one second exterior opening in the exterior surface at the distal end of the head in direct communication with the space outside of the head and in fluidic communication with the single gas-fillable lumen such that another portion of the gas supplied from the single gas-fillable lumen forms a secondary stream of gas directed longitudinally away from the at least one second exterior opening along the primary stream or at least partially peripherally around the primary stream;
an electrode disposed in the channel in or adjacent to the first exterior opening of the head for forming a plasma stream from the primary stream; and
wherein the channel is free of an electrode in the at least one second exterior opening and is free of an electrode adjacent to the at least one second exterior opening for forming a non-ionized stream of gas from the secondary stream such that the electrosurgical head is adapted to discharge the plasma stream and the non-ionized stream of gas into the space outside of the head with the non-ionized stream of gas along or at least partially peripherally around the plasma stream.

* * * * *